United States Patent [19]

Jimbow

[11] Patent Number: 5,756,068

[45] Date of Patent: May 26, 1998

[54] METHODS OF RADIOIMAGING AND RADIOCHEMOTHERAPY USING PHENOLIC THIOETER AMINES AND ACYL DERIVATIVES THEREOF

[75] Inventor: Kowichi Jimbow, Alberta, Canada

[73] Assignee: The Governors of the University of Alberta, Edmonton, Canada

[21] Appl. No.: 708,125

[22] Filed: Aug. 27, 1996

Related U.S. Application Data

[63] Continuation of Ser. No. 367,194, PCT/CA93/00292 Jul. 14, 1993.

[30] Foreign Application Priority Data

Jul. 15, 1992 [GB] United Kingdom ............... 9215066
Nov. 5, 1992 [CA] Canada ........................... 2082.252

[51] Int. Cl.$^6$ ............... A61K 51/04; C07C 323/25; C07C 323/41
[52] U.S. Cl. ............... 424/1.81; 424/1.85; 564/219; 564/340; 564/341
[58] Field of Search ............... 424/1.85, 1.65, 424/1.81, 422, 423, 712, 62; 514/630, 649; 564/219, 341, 340; 544/158, 85

[56] References Cited

U.S. PATENT DOCUMENTS

| | | |
|---|---|---|
| 4,134,996 | 1/1979 | Dunbar et al. |
| 4,183,927 | 1/1980 | Begin et al. |
| 5,283,342 | 2/1994 | Gustavson et al. ........ 548/304.1 |
| 5,395,611 | 3/1995 | Jimbow . |

FOREIGN PATENT DOCUMENTS

WO91/16302  10/1991  WIPO .

OTHER PUBLICATIONS

Synthesis of Cysteinylphenol, Cysteaminylphenol, and Related Compounds, and in Vivo Evaluation of Antimelanoma Effect by S. Miura, T. Ueda, K. Jimbow, S. Ito, K. Fujita—Arch. Dermatol. Res. 279:219–225, 1987.

Depigmentation of Back Guinea Pig Skin by Topical Application of Cysteaminylphenol, Cysteinylphenol, and Related Compounds by Y. Ito, K. Jimbow, S. Ito—J. Invest. Dermatol. 88:77–82, 1987.

Selective Cytotoxicity of 4–S–Cysteaminylphenol on Follicular Melanocytes of the Black Mouse: Rational Basis for Its Application to Melanoma Chemotherapy by Y. Ito, K. Jimbow—Cancer Res. 47:3278–3284, 1987.

Selective Cytotoxicity of N–acetyl–4–S–cysteaminylphenol on Follicular Melanocytes of Black Mince by M. Wong, K. Jimbow—Brit. J. Dermatol. 124:56–61, 1991.

Selective Cytotoxicity of a Phenolic Melanin Precursor, 4–S–Cysteaminylphenol, on in Vitro Melanoma Cells by K. Yamada, K. Jimbow, R. Engelhardt, S. Ito—Biochem Pharmacology 38:2217–2221, 1989.

The Synthesis of N–Acetyl–4–S–Cysteaminyl [U–$^{14}$C]Phenol as a Basis for the Development of an Antimelanoma and Melanomaradioimaging Agent by T. Iwashina, K. Jimbow, L. I. Wiebe—Appl Radiat Isot 45:703–705, 1994.

Reactivity of Orthoquinones Involved in Tyrosinase–Dependent Cytotoxicity: Differences Between Alkylthio– and Alkoxy–Substituents by C.J. Cooksey, K. Jimbow, E.J. Land, P.A. Riley—Melanoma Res 2:283–293, 1992.

Phenolic Melanin Precursors Provide a Rational Approach to the Design of Antitumor Agents for Melanoma by K. Jimbow, T. Miura, S. Ito, K. Ishikawa—Pigment Cell Res 2:34–39, 1989.

Jimbow et al., "Exploitation of Pigment Biosynthesis Pathway as a Selective Chemotherapeutic Approach for Malignant Melanoma," *The Journal of Investigative Dermatology*, vol. 100, No. 2, Feb. 1993, pp. 231S–238S.

4–S–Cysteaminylphenol and its Analogues as Substrates for Tyrosinase and Monoamine Oxidase by J.M. Pankovich, K. Jimbow, S. Ito—Pigment Cell Res 3:146–149, 1990.

Experimental Antimelanoma Agents: The Synthesis of 4–S–Cysteaminyl [U–$^{14}$C]phenol by VV Somayaji, LI Wiebe, K. Jimbow—Current Contents and Excerpta Medica 20:158–159, 1989.

Mechanism of Growth Inhibition of Melanoma Cells by 4–S–Cystteaminylphenol and its Analogues by S. Inoue, S. Ito, K. Wakamatsu, K. Jimbow, K. Fujita—Biochem Pharmacol 39:1077–1083, 1990.

Melanocytotoxicity and Antimelanoma Effects of Phenolic Amine Compounds in Mice in Vivo by F. Alena, K. Jimbow, S. Ito—Cancer Research 50.3743–3747 Jun. 15, 1990.

N–Acetyl–4–S–cysteaminylphenol as a New Type of Depigmenting Agent for the Melanoderma of Patients with Melasma by K. Jimbow—Arch Dermatol 172:1528–1534, 1991.

Action of Cysteaminylphenols on Human Melanoma Cells in Vivo and in Vitro: 4–S–Cysteaminylphenol Binds Protein Disulphide Isomerase by P.G. Parsons, D. Favier, M. McEwan, H. Takahashi, K. Jimbow, S. Ito—Melanoma Res 1:97–104, 1991.

Selective in Vivo and in Vitro Incorporation and Accumulation of Phenolic Thioeter Amine into Malignant Melanoma and Indentification of a (58 kD) Binding Glycoprotein by K. Yamada, K. Jimbow—Melanoma Res 2:225–233, 1992.

Glutathione Plays a Key Role in the Depigmenting and Melanocytotoxic Action of N–Acetyl–4–S–Cysteaminylphenol in Black and Yellow Hair Follicles by F. Alena, W. Dixon, P. Thomas, K. Jimbow—J. Invest Dermatol 104:792–797, 1995.

Selective in Vivo Accumulation of N–Acetyl–4–S–Cysteaminylphenol in B16F10 Murine Melanoma and Enhancement of its in Vitro and in Vivo Antimelanoma Effect by Combination of Buthionine Sulfoximine by F. Alena, T. Iwashina, A. Gili, K. Jimbow—Cancer Res 54:2661–2666, 1994.

(List continued on next page.)

*Primary Examiner*—Gary E. Hollinden
*Assistant Examiner*—Michael G. Hartley

[57] ABSTRACT

Compounds useful in radioimaging and radiochemotherapy as it particularly relates to the treatment and location of malignant melanomas and other pigmenting disorders, as well as novel acyl derivatives of phenolic thioester amines and their use in compositions for blocking melanin synthesis in human or animal melanocyte cells.

10 Claims, No Drawings

OTHER PUBLICATIONS

The in Vivo Melanocytotoxicity and Depigmenting Potency of N–2,4–Acetoxyphenyl Thioethyl Acetamide in the Skin and Hair by M. Jimbow, H. Murusyk, K. Jimbow—British J. Dermatol (in press), 1995.

The in Vivo Antimelanoma Effect of 4–S–Cysteaminylphenol and its N–Acetyl Derivative by T. Miura, K. Jimbow, S. Ito—Int. J. Cancer 46:931–934, 1990.

Malignant Melanoma: A Life Threatening Skin Cancer Affecting Young People—Its Diagnosis and Management by G.J. Lauzon, K. Jimbow—Am Royal Col Phys Surg 23:105–110, 1990.

Electron Donor and Acceptor Properties of Melanin Pigments in the Skin by K. Reszka, K. Jimbow—In: Oxidative Stress in Dermatology, ed by Fuchs J and Packer J. Marcel Dekker Inc., New York, pp. 287–320, 1993.

METHODS OF RADIOIMAGING AND RADIOCHEMOTHERAPY USING PHENOLIC THIOETER AMINES AND ACYL DERIVATIVES THEREOF

This is a continuation of application Ser. No.08/367,194, filed Mar. 15, 1995.

FIELD OF THE INVENTION

This invention relates to compounds which are particularly useful in radioimaging and radio-chemotherapy as it particularly relates to the treatment and location of malignant melanomas and other pigmenting disorders. Novel acyl derivatives of phenolic thioether amines and their use in compositions for blocking melanin synthesis in human or animal melanocyte cells are also described. More particularly, the compositions involving the novel derivatives are useful in treating pigmentation problems due to a variety of skin disorders, including skin cancer in the form of melanoma.

BACKGROUND OF THE INVENTION

Phenylthioalkylazines is a broad class of compounds having a variety of uses which include therapeutics. U.S. Pat. Nos. 4,134,996 and 4,183,927 disclose certain phenylthioalkylamine compounds which are useful as platelet aggregation inhibitors. Other phenylthioalkylamine compounds of applicant's published International application WO91/16302 are useful as depigmenting agents in treating a variety of pigmentary diseases. Such diseases are often characterized in the elevated levels of the enzyme tyrosinase in melanocytes; i.e., human and animal cells which synthesize the pigment melanin. There are a variety of pigmentary diseases, such as melasma, melanoma, moles and the like. In particular, moles are susceptible to becoming melanoma after exposure to sunlight which precipitates increased synthesis of tyrosinase.

Usually commercial forms of depigmenting compositions are based on the use of hydroquinone. However, the hydroquinone preparations are very unstable and cause skin irritation. Hydroquinone compositions can also cause permanent whitening of the skin if used for a prolonged period and at a high concentration. As to treatment of melanoma, this is presently attended to by surgical procedures, since any type of known non-surgical treatment of melanoma is unsatisfactory.

Research work has been conducted in the field of phenolic and diphenolic compounds to serve as a basis for chemotherapeutic treatment of melanoma and skin depigmentation. In particular, 4-S-cysteinylphenol (4-S-CP) and 4-S-cysteaminylphenol (4-S-CAP) have been synthesized and evaluated for cytotoxicity to normal epidermal melanocytes to determine their effectiveness as depigmenting agents and antimelanoma agents. Miura et al, "Synthesis of Cysteinylphenol, Cysteaminylphenol, and Related Compounds, and In Vivo Evaluation of Antimelanoma Effect", Arch. Dermatol Res. (1987) 279:219–225, disclose the effect of 4-S-CAP and 4-S-CP in depigmentation of black hair follicles as manifested by loss of functioning melanocytes. It was established that 4-S-CAP was a potent agent in prolonging the lifespan of melanoma-bearing mice and hence exhibited inhibition of melanoma growth. 4-S-CP and the methyl ester of 4-S-CP also exhibited some inhibition of melanoma growth, although not as active as 4-S-CAP.

The same compounds, 4-S-CP and 4-S-CAP, were also investigated for properties of depigmentation of black guinea pig skin by topical application. The results of this work is reported by Ito et al, "Depigmentation of Black Guinea Pig Skin by Topical Application of Cysteaminylphenol, Cysteinylphenol, and Related Compounds", The Journal of Investigative Dermatology, Vol. 88 No. 1, January 1987. Although 4-S-CAP demonstrated depigmenting properties, inflammatory changes of the skin of the guinea pigs was prominent. 4-S-CAP was capable, however, of:

1. decreasing the number of functioning melanocytes;
2. decreasing the amount of epidermal melanin pigments; and
3. degenerating and destroying melanocytes.

4-S-CP and 4-S-CAP were also investigated for their selective cytotoxicity on follicular melanocytes. This was reported by Ito et al, "Selective Cytotoxicity of 4-S-Cysteaminylphenol on Follicular Melanocyte of the Black Mouse: Rational Basis for its Application to Melanoma Chemotherapy", Cancer Research, Jun. 15, 1987 47:3278–3284. It was reported that 4-S-CAP demonstrated cytotoxicity in the depigmentation of black hair follicles, whereas it had no effect on the albino follicles. Hence 4-S-CAP is actively engaged in the melanin synthesis of the melanocytes.

4-S-CAP, however, has several limitations from the standpoint of practical clinical use. These limitations include:

a. hypotensive-effect; and
b. high toxicity due to 4-S-CAP being a substrate for monoamineoxidase (MAO) which in the plasma converts 4-S-CAP into an aldehyde form which produces a non-specific cytotoxicity.

Homologs of 4-S-CAP have been investigated for antimelanoma and depigmenting properties. As reported in Alena et al, Melanocytotoxicity and Antimelanoma Effects of Phenolic Amine Compounds in Mice In Vivo, Cancer Research 50:3743–3747, Jun. 15, 1990, such homologs demonstrate depigmentation properties and N-acetyl-4-S-CAP demonstrates potent antimelanoma properties. The benefits and uses of these homologs and related compounds for use as depigmenting agents and antimelanoma agents are described in applicant's published International application WO 91/16302. Although the compounds disclosed in that application are effective depigmenting agents as well as antimelanoma agents, there are stability and toxicity problems associated with some of the compounds. In particular the very effective N-acetyl- 4-S-CAP compound tends to be unstable and can cause topical irritations on administration.

As noted, melanin synthesis is a biological property unique to the pigment cell, melanocyte and its neoplastic counterpart, malignant melanoma. In order to develop a targeted chemotherapy of malignant melanoma, phenolic and catecholic melanin precursors have been synthesized and their melanocytotoxicity and antimelanoma effects have been examined (Ito, Y. et al, 1987; Miura, S. et al, 1987; Alena, F. et al, 1990; Jimbow, K. et al, 1992). Among these, S-substituted phenolic amines, N-acetyl-4-S-cysteaminylphenol (N-Ac-4-S-CAP) was found to be a superior substrate of melanin synthesizing enzyme, tyrosinase (Pankovich, J. et al, 1990; Miura, T. et al, 1990), and to possess the most effective melanocytotoxic activity and antimelanoma effect (Miura, T. et al, 1990; Alena, F. et al, 1990; Wong, M. et al, 1991). 4-S-CAP was, however, as noted, above, found to have some general cytotoxicity (Alana, F. et al, 1990), because it is metabolically transformed to a cytotoxic aldehyde metabolite by plasm monoamine oxidase (Pankovich, J. et al; Inoue, S. et al, 1990). On the other hand, N-Ac-4-S-CAP has shown an absence of such cytotoxicity (Alena, F. et al, 1990), indicating that N-Ac-4-S-CAP may be a compound suitable for the development of melanoma chemotherapy.

In the treatment of various pigmentary disorders, it would also be beneficial to determine the specificity of the compounds used in the treatment and in particular, compounds such as N-Ac-4-S-CAP. In this regard, we have also discovered that certain anti-melanoma and depigmenting agents can be labelled with radioactive molecules to achieve not only radioimaging but as well, radio-chemotherapy particularly in the treatment of malignant melanoma.

In accordance with this invention, we have also discovered esterified compounds which exhibit excellent stability and very low general toxicity, but have selective toxicity for melanocytes.

SUMMARY OF THE INVENTION

In accordance with one aspect of the invention, there is provided a compound for use in radioimaging and radio-chemotherapy in the diagnosis and/or treatment of melanoma and other pigmentary disorders, said compound being selected from the group of compounds represented by the formula:

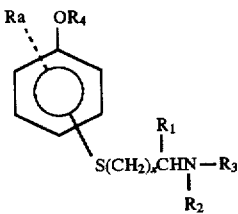

wherein $R_1$ is H or $C_1$–$C_8$ alkyl;

$R_2$ is H or $C_1$–$C_8$ alkyl;

$R_3$ is H, $C_1$–$C_8$ alkyl or $C_1$–$C_8$ alkanoyl;

$R_4$ is H or $C_1$–$C_8$ alkanoyl;

Ra is a radioactive material useful in radioimaging and/or radiochemotherapy where the dotted line ( - - - ) indicates:

1) Ra is covalently bound to the structure of formula (I);
2) Ra is ionically associated with the structure of formula (I); or
3) Ra is radioactive carbon which is part of the structure of formula (I);

and x is 1 to 5, with the provisos that when x is 1, one of $R_1$, $R_2$ or $R_3$ is other than H, and that the sulphur containing group and the Ra group are in the 2, 4 or 6 positions of the phenyl ring.

In accordance with a further aspect of the invention, there is provided a process for radioimaging melanoma colonies in vivo in a subject comprising:

i) administering to the subject's circulatory system one or more radioimaging compounds selected from the group of compounds represented by the formula:

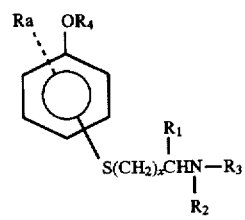

wherein $R_1$ is H or $C_1$–$C_8$ alkyl;

$R_2$ is H or $C_1$–$C_8$ alkyl;

$R_3$ is H, $C_1$–$C_8$ alkyl or $C_1$–$C_8$ alkanoyl;

$R_4$ is H or $C_1$–$C_8$ alkanoyl;

Ra is a radioactive material useful in radioimaging and/or radiochemotherapy where the dotted line ( - - - ) indicates:

1) Ra is covalently bound to the structure of formula (I);
2) Ra is ionically associated with the structure of formula (I); or
3) Ra is radioactive carbon which is part of the structure of formula (I);

and x is 1 to 5, with the provisos that when x is 1, one of $R_1$, $R_2$ or $R_3$ is other than H, and that the sulphur containing group and the Ra group are in the 2, 4 or 6 positions of the phenyl ring;

and ii) detecting the presence of emitted radiation from an accumulation of said selected radioimaging compound as said administered compound binds solely to any melanoma tissue present in said subject.

In accordance with another aspect of the invention, there is provided a process for radiochemotherapy treatment of melanoma cells in a subject comprising:

i) administering to the subject's circulatory system one or more of the radiochemotherapy compounds selected from the group of compounds represented by the formula:

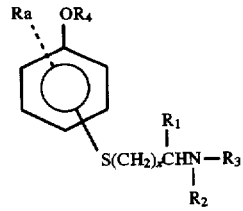

wherein $R_1$ is H or $C_1$–$C_8$ alkyl;

$R_2$ is H or $C_1$–$C_8$ alkyl;

$R_3$ is H, $C_1$–$C_8$ alkyl or $C_1$–$C_8$ alkanoyl;

$R_4$ is H or $C_1$–$C_8$ alkanoyl;

Ra is a radioactive material useful in radioimaging and/or radiochemotherapy where the dotted line ( - - - ) indicates:

1) Ra is covalently bound to the structure of formula (I);
2) Ra is ionically associated with the structure of formula (I); or
3) Ra is radioactive carbon which is part of the structure of formula (I); and x is 1 to 5, with the provisos that when x is 1, one of $R_1$, $R_2$ or $R_3$ is other than H, and that the sulphur containing group and the Ra group are in the 2, 4 or 6 positions of the phenyl ring.

In accordance with another aspect of the invention, the preferred compounds of formula (I) are when X is 1 and $R_4$ is alkanoyl.

In accordance with another aspect of the invention, a compound of the formula (II):

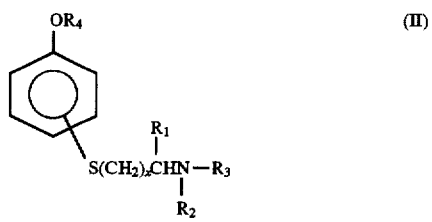

wherein $R_1$ is H or $C_1$–$C_8$ alkyl;

$R_2$ is H, $C_1$–$C_8$ alkyl or $C_1$–$C_8$ alkanoyl;

$R_3$ is H or $C_1$–$C_8$ alkyl;

$R_4$ is $C_1$–$C_8$ alkanoyl; and x is 1 to 5;

with the proviso that when x is 1 one of $R_1$, $R_2$ or $R_3$ is other than H, and that the sulphur containing group is in the 2, 4 or 6 position of the phenyl ring.

In accordance with another aspect of the invention, the preferred compounds of formula (II) are when x is 1 and $R_4$ is alkanoyl.

In accordance with a further aspect of the invention, a pharmaceutical composition comprises a compound of formula (II) and a pharmacologically or biologically acceptable carrier.

According to a preferred aspect of the invention, this composition is particularly useful as a depigmenting composition in sunscreening lotions. The composition is also useful as an antimelanoma agent and useful for the treatment of melasma.

In accordance with another aspect of this invention, a composition useful for blocking melanin synthesis in human or animal melanocyte cells, comprises:

i) a biologically effective amount of an active compound selected from the group represented by formula (II); and ii) a suitable biologically compatible carrier for the selected active compound.

According to another aspect of the invention, a method for blocking melanin synthesis in human or animal melanocyte cells comprises treating human or animal skin by use of a composition comprising a biologically effective amount of an active compound selected from the group represented by formula (II).

Such methods of treatment are preferably applied in the depigmenting of skin due to UV exposure, melasma and is also useful in the treatment of melanoma.

According to another aspect of the invention, there is provided a method of formulating a composition useful for blocking melanin synthesis in human or animal melanocyte cells of skin comprises mixing:

i) a biologically effective amount of an active compound selected from the group represented by formula (II); and ii) a suitable biologically compatible carrier.

DETAILED DESCRIPTION OF THE PREFERRED EMBODIMENTS

The radiolabelled compounds of this invention are capable of binding to melanoma tissue such that when the tissue is subjected to radioimaging the existence of such melanoma colonies or cells appears in the image. Further, by virtue of the binding of these compounds to melanoma sites, the radioactive material may be used in radiochemotherapy treatment of the melanoma cells to either kill such cells or effect their remission.

The preferred compounds of this invention exhibit considerably less toxicity than known forms of phenolic amine compounds such as the aforementioned 4-S-CP and 4-S-CAP. In particular, when 4-S-CAP is used in radioimaging or radiochemotherapy, the compound collects in the eye as well as in the melanoma tissue. However, the compounds of formula (I) do not have such drawbacks and are therefore particularly suited to this new use. When the compounds of the formula (I) are used in radiochemotherapy they may be combined with suitable pharmaceutical excipients and carriers wherein the radioactive selected compounds are present in a biologically effective amount in the carriers. Suitable biologically, compatible carriers may be solutions when injected by either the IP or SC route. Suitable biologically, compatible carriers for injection include physiologically normal saline and other types of readily injectable solutions which are well understood by those skilled in the art and readily available. The preferred injectable carrier is a neutral buffer having a pH of 7 to 7.4 and does not in any way effect the activity of the radiolabelled compounds. For purposes of injection, the concentration of the radiolabelled compound in the injectable solution is normally in the range of 200 to 1200 mg per kg of body weight where the preferred dosage is in the range of 300 mg to 500 mg per kg of body weight. In the following examples, further information is provided as to the amount of compounds injected for purposes of radioimaging.

Although one skilled in the art appreciates that there are a variety of techniques for making the compounds of formula (I) before they are radiolabelled the proposed method for manufacturing the compounds is via the Weirmeister reaction as described in WO 91/16302.

As will be demonstrated in the following examples, radiolabelled compounds of this invention bind specifically to melanoma tissues and the radiolabelled compound or radiolabelled derivatives thereof remain in the melanoma tissue for a sufficient period of time for either therapeutic treatment or for subsequent radioimaging. The radiolabelling of the compound occurs normally in the phenyl ring in accordance with the following reaction schemes.

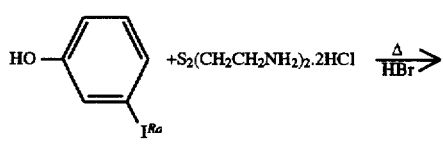

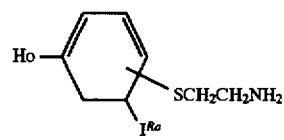

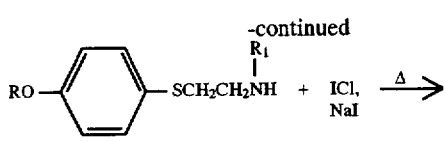

R = H, R₁ = Acetyl: N—Ac-4-S-CAP
R—R₁-Acetyl: NAP-TEA

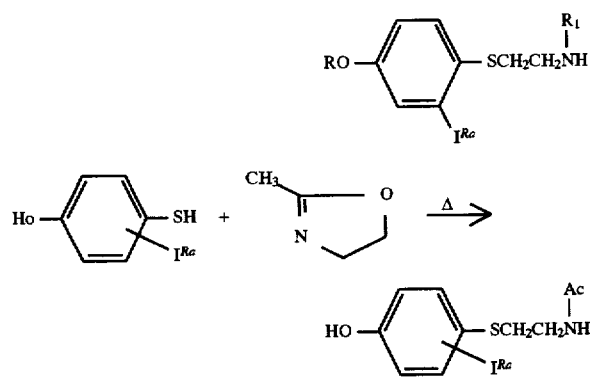

wherein $I^{Ra}$ is a radioactive form of iodine.

Exemplary iodine labelling is as follows:
N-acetyl-3-iodo-4-S-cysteaminyl-phenol;
N-acetyl-2-S-cysteaminyl-3-iodo-phenol;
N-acetyl-2-S-cysteaminyl-5-iodo-phenol;
N-{2-{(2'-iodo-4'-acetoxy-phenyl)thio}ethyl}acetamide;
N-{2-{(2'-acetoxy-5'-iodo-phenyl)thio}ethyl}acetamide; and
N-{2-{(2'-acetoxy-3'-iodo-phenyl)thio}ethyl}acetamide.

Various radiolabelling agents may be used such as carbon 14, U-14-C, iodine (such as $^{123}I$, $^{125}I$ and $^{131}I$), technetium (such as $^{99m}Tc$), Flourine (such as $^{18}F$), indium (such as $^{111}In$) and $S^{35}$ for example. The method of introduction of the radiolabelling agent to the compound will depend on the choice of radiolabelling agent, as one skilled in the art would appreciate. The radiolabelling agent will be associated with the structure of the compound through one of the several ways: (1) through a covalent bond with the compound structure; (2) through ionic association with the compound structure; or (3) as part of the structure of the compound.

Novel acylated compounds of this invention are represented by the compounds of formula (II). It has been found that those compounds are particularly useful in the treatment of various pigmentation disorders and, when formulated into suitable pharmaceutical compositions, exhibit excellent stability and very low general toxicity, but selective toxicity with respect to melanocytes. Hence, in accordance with another aspect of this invention, the pharmaceutical compositions are very useful in the treatment of pigmentary diseases such as treatments involving one or more of the following:

blocking melanin synthesis in human or animal melanocyte cells, inhibiting the metabolic pathway involving tyrosinase in human or animal melanocyte cells, and treatment of melanoma, treatment of hyperpigmentation and treatment of cutaneous hyperpigmentation.

In formulae (I) and (II), preferred lower alkyl and lower alkanoyl groups are $C_1$ to $C_6$. The most preferred lower alkyl and lower alkanoyl groups are $C_1$ to $C_4$.

Preferred compounds of formula (I) include N-acetyl-4-S-cysteaminylphenol, N,N-dimethyl-4-S-cysteaminylphenol, 4-S-homo-cysteaminylphenol, α-methyl-4-S-cysteaminylphenol, N-{2-{(4'-acetoxyphenyl)-thio}ethyl}acetamide, N-{1-methyl{2-{(4'-acetoxyphenyl)thio}ethyl}acetamide, N,N-dimethyl (2-{(4'-acetoxyphenyl)thio}ethylamine or N-propionyl-4-S-cysteaminylphenol.

Preferred specific compounds of the invention of Formula (II) are:

| Compound | R₁ | R₂ | R₃ | R₄ |
|---|---|---|---|---|
| 1. N-(1-Methyl-{2-{(4'-acetoxyphenyl)thio}-ethyl}acetamide | CH₃ | H | COCH₃ | COCH₃ |
| 2. N,N-Dimethyl {2-{(4-acetoxyphenyl)thio}-ethylamine | H | CH₃ | CH₃ | COCH₃ |
| 3. N-{2-{(4'-acetoxyphenyl)thio}ethyl}-acetamide | H | H | COCH₃ | COCH₃ |
| 4. N-{2-{(4-acetoxyphenyl)-thio}ethyl)propionamide | H | H | COC₂H₅ | COCH₃ |

The compounds of formula (II) may be manufactured by a variety of synthesis techniques. Generally, they may be prepared by acylation of the corresponding cysteaminylphenol compounds.

The cysteaminylphenol compounds may also be prepared in accordance with the technique disclosed by Miura et al, "Synthesis of Cysteinylphenol, Cysteaminylphenol, and Related Compounds, and in vivo Evaluation of Antimelanoma Effect", Arch. Dermatol. Res. (1987) 279:219–225. This entails the reaction of a phenol with a cysteamine to yield 4-S-cysteaminylphenol or 2-S-cysteaminylphenol. 4-S-cysteaminylphenol may then be isolated from the reaction product by Silica gel column chromatography or crystallization with changing pH of solution. It is understood that the various derivatives of this invention may be made by various radical substitutions to the sulphur chain, or substituting a thiol with the desired chain.

Details of processes for making some of the preferred compounds of the invention are set out in the accompanying Examples.

The intermediate cysteaminylphenol compounds may be acylated by reaction with the appropriate alkanoyl; for example, acetyl chloride may be reacted with N-{2-((4-hydroxyphenyl)thio)ethyl}acetamide, to give the preferred compound of the invention N-{2-((4'-acetoxyphenyl)thio) ethyl}acetamide (NAP-TEA).

The compositions of this invention having active agents of formula (II) provide a mechanism for treating a variety of pigmentary diseases, such as melasma and other hyperpigmentation diseases and melanoma and other skin cancers and for preventing melasma and skin cancers which are normally induced by exposure to UV radiation. This activity of the composition is achieved by the selected active compound of the composition becoming toxic in the melanocytes in the presence of tyrosinase without being a substrate for plasma MAO. The compositions upon administration, according to this invention, have significant melanoma cytotoxicity and antimelanoma effects. This is recognized in the significant depigmentation of hair on black experimental animals, as well as significantly inhibiting the experimental growth of lung metastases of B16 F10 melanoma cells. The compositions of this invention have also demonstrated selective toxicity to other neural crest tumors, such as pheochromocytoma and neuroblastoma cells.

Experimental tests on animals indicate per single dose toxicity levels in the range of 1,400 mg/kg of body weight for the preferred compound of formula (II), NAP-TEA.

In the pharmaceutical compositions of the invention, the term "a biologically effective amount of the active compound" means that a sufficient amount of the compound in the composition is provided such that upon administration to the human or animal by, for example, i.p., s.c. or topical route provides sufficient active agent on each application to give the desired result in treating various pigmentary diseases, including melanoma, melasma, or acting as UV blocker and/or depigmenting agent in sunscreen lotions. However, the biologically effective amount of the active compound is at a level that it is not toxic to the human or animal during the term of treatment.

The term "a suitable biologically compatible carrier" includes a solvent for the compound when the compound is injected by either i.p. or s.c. route. Suitable biologically compatible carriers for injection include physiologically normal saline and other types of readily injectable solutions which are well understood by those skilled in the art. The preferred injectable carrier is a neutral buffer having a pH of 7.0 to 7.4. When the compound is topically applied, the carrier may be any type of suitable excipient or carrier in the form of cosmetic compositions, pharmaceutical adjuvants, sunscreen lotions and the like.

Suitable carriers for topical application include conventional skin treatment compositions, such as cosmetic compositions and pharmaceutical preparations. Examples of such ingredients for topical application are oils such as liquid paraffin, vaseline, methylpolysiloxane, castor oil, squalane, and coconut oil; anti-oxidants such as butylated hydroxyanisole, butylhydroxytoluene, ethyl gallate, and tocopherol; surfactants such as sodium laureate, laurylpyridinium chloride, polyoxyethylene sorbitan monooleate, glyceryl monoarachate, sodium N-stearyl-N,N-dimethyl glycine, oleyl hydrolysed animal protein, and polyoxypropylene glyceryl ether phosphate; humectants such as glycerol, sodium 2-pyrrolidone-5-carboxylate, and sodium lactate; thickeners such as tragacanth gum, quince seed gum, zanthan gum, carboxyvinyl polymer and bentonite; preservatives such as benzoic acid, allyl p-hydroxybenzoates, dehydroacetic acid and trichlorocarbonilide; coloring agents and pigments such as Acid Red Rhodamine B, Violamin R, Orange SS, Naphthol, Yellow-S, Tartrazine, Alizarin, Cyanine Green F, Brilliant Blue CFC, Acid Violet, Carthamine, β-carotene, Red, Blue & Yellow Oxide of Iron, titanium dioxide, Yellow Iron Oxide, Cobalt Blue, Ultramarine Blue, Rose & Violet, tri-iron tetroxide, and carbon black; waxes such as Bees wax, Japan wax, Carnauba wax, Candelilla wax, and lanolin; film-forming agents such as nitrocellulose and polyvinyl alcohol; solvents or dispersing media such a water and alcohols (e.g. ethanol); powders such as aluminum powder, talc, kaolin, zinc oxide, titanium dioxide, mica, calcium, carbonate, and treated powders; plasticizers such as acetyl tributyl citrate, and dibutylphthalate; pharmaceutically active agents such as retinol, palmitate; γ-orizanol, pyridoxine dipalmitate, ascrobyl dipalmitate, ergocalciferol, di-α-tocopherol acetate, biotin, ethinylestradiol estrone, hydrocortisone, calcium pantothenate, ammonium glycyrrhizinate, allantoid, quaiasulene, and hinokitiol; and perfumes such as musk, civet, amber, jasmine absolute, and rose oil.

The skin treatment compositions, according to this invention, can be prepared in any conventional form, for example, solubilized forms such as cosmetic lotions, and emulsified forms such as liquid creams, creams, ointments and dispersions.

The pharmaceutical compositions of this invention are particularly useful for depigmenting skin where the composition is applied topically or injected by s.c. or i.p. route to the afflicted area to achieve desired degree of depigmentation-of the skin. Hence as another aspect of the invention, the composition is useful in the method of treating skin for purposes of depigmentation. As well, the invention provides for formulating a composition which is useful for depigmenting skin.

The compositions of the invention are also especially useful for treating melanoma. The composition is administered either topically or by injection through i.p. or s.c. route. The composition is used in treating melanoma to either clear it up or place it in remission. Furthermore, a method of the invention is in the formulating of the composition useful for treating melanoma.

The compounds of formula (II) may be used in sunscreening lotions as depigmenting agents. It has been found that the active agents of formula (II):

1. prevent UV radiation activating melanin synthesis in melanocytes;
2. prevent moles from becoming melanoma after exposure to sunlight; and
3. are substrates for the enzyme tyrosinase where it is thought that enzymatic conversion of the substrates produce components which act as depigmenting agents and possibly as UV blockers in the sunscreen lotion.

Quite surprisingly, we have found that, upon administration of the acylated derivatives of formula (II), the compounds are deacylated to become potent melanocytotoxic and depigmenting agents. Such in vivo conversion of the compounds is extremely beneficial from the standpoint of product stability and reduced general toxicity. Once the compounds of formula (II) are deacylated upon administration, they become excellent tyrosinase substrates. According to a preferred embodiment of the invention, NAP-TEA, once incorporated into the body, is deacylated to become N-acetyl-4-S-CAP which is, as already demonstrated in the aforementioned International Application WO91/16302, a strong tyrosinase substrate that is present only in pigment cells. This enzyme activity becomes highly expressed in malignant melanoma and melasma cells where the specificity of N-acetyl-4-S-CAP is important in avoiding general toxicity to the patient. The therapeutic approach in the use of these compounds for pigmentary diseases such as melasma and skin cancer, such as malignant melanoma, have become very important as well as preventive medicine for photoaging and skin cancer developed after exposure to sunlight. Melanoma represents 2% of all cancer by instance and is generally increasing in the population at a rate exceeded only by lung cancer.

For purposes of treatment, it is understood that depending upon the route of administration the composition of this invention may have various concentrations of active agent in the biologically compatible carrier. For purposes of injection, the concentration of the active agent in the injectable solution usually is in the range of 200 to 1200 mg/kg of body weight with a preferred dosage in the range of 300 mg to 500 mg/kg of body weight. For purposes of topical application, the concentration of the active agent in the cosmetic cream or the like usually is in the range of 4% to 10% by weight in a cream base with a preferred composition in the range of 4% to 6% by weight in a cream base.

It is appreciated that various complementary agents may be included with the active agents of this invention. For example, the composition may be administered in combination with L-dopa and/or antidecarboxylase. Such combinations may have selected use in the treatment of various melanomas.

The following Examples demonstrate various aspects of the invention in providing the diagnosis and treatment of pigmentation diseases, depigmenting properties and antimelanoma properties. The various compounds of formula (I) may be radiolabelled in accordance with a preferred procedure outlined in the following Examples. The procedures have been described in particular reference to the compound N-acetyl-4-S-CAP; however, it is understood that the procedure may be similarly applied to the other compounds of formula (I). Furthermore, the Examples also demonstrate effectiveness in blocking melanin synthesis for only one of the compounds of formula (II). However, it is understood that the compounds of formula (II) all exhibit in a predictable way similar properties.

EXAMPLE 1

Synthesis of N-Acetyl-4-S-cysteaminyl (U-$^{14}$C) Phenol (U-$^{14}$C)phenol (9.26 MBq, 333.3 MBq/mmol) in toluene (0.25 mL) was added to aqueous HBr (47% w/v; 0.5 mL solution containing unlabelled phenol (1.7 mg; 0.018 mmol) and cystamine.2HCl (45 mg; 0.2 mmol). The mixture was heated for 30 min at 130° C. in a screw-capped reaction vial. After cooling, the solvent was removed under vacuum and the residue was dissolved in aqueous methanol (3% v/v). The solution was applied to a Sep-Pak $C_{18}$ cartridge. The cartridge was washed with aqueous methanol (10% v/v; 0.6 mL for removal of excess cystamine and ($^{14}$C) labelled 4-S-CAP and 2-S-CAP were eluted with aqueous methanol (20% v/v; 3.0 mL). The eluent was concentrated under vacuum. The major compounds were separated on preparative TLC using the mobile phase I. The products were extracted from TLC with MeOH in $CHCl_3$ (20% v/v). The two isomers were acetylated with acetic anhydride in dry pyridine at 25° C. for 24 hours. The solvent was removed under vacuum. The residue was dissolved in $NH_3$ (2.0M) and stirred at 25° C. for 30 min for O-deacetylation. After reaction, the methanol solvent was removed under vacuum and the residue was purified on preparative TLC using mobile phase II. ($^{14}$C)N-Ac-4-S-CAP (9.5 µCi, 351.9 kBq) and ($^{14}$C)N-Ac-2-S-CAP(5.7 µCi, 211.1 kBq) in 3.8% and 2.3% radiochemical yield respectively. The radiochemical purity of the two isomers was more than 99%.

This Example demonstrates that one is able to synthesize ($^{14}$C)N-Ac-4-S-CAP with conventional acetylation and O-deacylation after electrophilic substitution on phenol of the $NH_2CH_2CH_2S^+$ cation in HBr solution, as per the following reaction scheme.

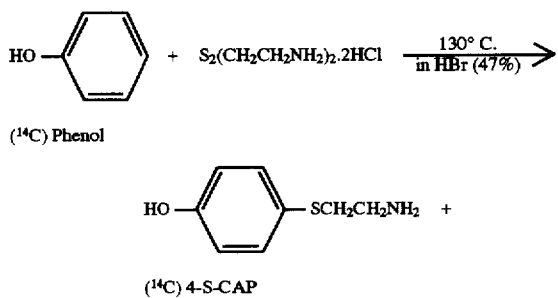

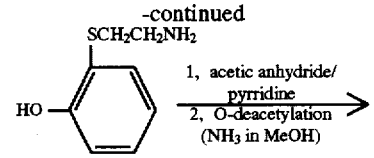

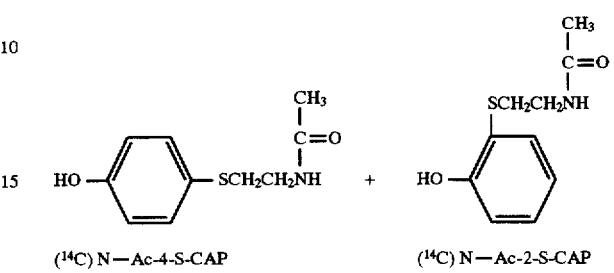

In the above reaction process, ($^{14}$C)-acetyl-2-S-cysteaminylphenol (($^{14}$C)-Ac-2-S-CAP was also obtained as a minor isomer. The synthesis of ($^{14}$C)4-S-CAP using the above reaction was as described previously (Somayaji et al, 1989). It was difficult to remove cystamine by methanol precipitation or to separate the 2 and 4 isomers of CAP by TLC system. However, it was possible to remove cystamine and accomplish preliminary purification using a Sep-pak $C^{18}$ cartridge. The chromatographic separation of the two isomers was accomplished with mobile phase I. This basic mobile phase allowed a complete separation of the two isomeric CAP compounds of the reaction mixture (4-S-CAP: Rf=0.66; 2-S-CAP: Rf=0.53).

Unlabelled crystalline phenol (2 mg) reacted smoothly with cystamine in HBr solution in a small scale reaction. An overall yield-was approximately 76% as a mixture of the two isomers, the ratio of 4-S-CAP to 2-S-CAP being 2.5. Acetylation of the O-position and the N-position on isomers was carried out with acetic anhydride in dry pyridine. O-Deacetylation for the synthesis of N-Ac-4-S-CAP was performed with $NH_3$ in methanol (2.0M) under mild conditions without N-deacetylation. A mixture of 4-S-CAP (a major product) and 2-S-CAP (a minor product) containing the $^{14}$C-radiolabel were obtained by using a two phase reaction system (toluene:HBr) under reflux, and with the addition of unlabelled phenol this gave low yield of products. If a source of (U$^{14}$C) phenol were available as a solid material or as a more concentrated solution, the yield and the specific activity can be greatly increased. ($^{14}$C)N-Ac-4-S-CAP synthesized from ($^{14}$C)4-S-CAP gave a high radiochemical yield (68%). Although the specific activity of ($^{14}$C )N-Ac-4-S-CAP and ($^{14}$C)N-Ac-2-S-CAP was low (450 kBq/µmol), the products would be sufficient to carry out experimental studies. The use of solid (U$^{14}$C) phenol with a high specific activity for the synthesis of ($^{14}$C)4-S-CAP and ($^{14}$C)2-S-CAP would increase both the specific activity and the yield of the final products.

All chemicals used were of reagent grade quality. (U-$^{14}$C) Phenol in toluene was purchased from Sigma Chemical Company (Saint Louis, Mo., USA). Preliminary purification was performed on Sep-Pak $C_{18}$ Cartridges (Waters Chromatography Division, Millipore Corporation, Milford, USA). Whatman PLK5F preparative silica gel 150A plates were used for separation of 4-S-cysteaminyl (U-$^{14}$C)phenol, ($^{14}$C) 4-S-CAP and 2-cysteaminyl (U-$^{14}$C) phenol (($^{14}$C)2-S-CAP) using mobile phase I ($CHCl_3$ MeOH: $NH_4OH$= 24:12:1.1 v/v/v) and using mobile phase II ($CHCl_3$:MeOH= 85 15 v/v) for the purification of the N-acetyl derivatives of the two isomers. $^{14}$C-Radioactivity determination of products was performed in Aquasal®-2 (Biotechnology Systems NEN® Research Product, Boston, Mass., USA) with a Beckman LS 3801 liquid scintillation spectrometer. HPLC analyses were carried out with a Waters system consisting of a Model 600E system controller, Model U6K injector and Model 441 detector at 254 nm, using µBonapak $C_{18}$ reverse phase compression (10µ) column (Waters Millipore Canada Ltd., Mississauga, Ontario) and MeOH:0.1% acetic acid in $H_2O$ (1:1 v/v) as eluent with a flow rate of 1 mL/min. The final products, N-acetyl-4-S-cysteaminyl (U-$^{14}$C) phenol (($^{14}$C) N-Ac-4-S-CAP) and N-acetyl-2-S-cysteaminyl (U-$^{14}$C)phenol (($^{14}$C) N-Ac-2-S-CAP) were confirmed by comparing their retention times to those of authentic unlabelled compounds on HPLC. Radiochemical purity after TLC was determined by collect eluent fractions (0.5 mL) from an HPLC analysis and counting by a liquid scintillation spectrometer.

EXAMPLE 2A

Synthesis of N-{2-((4-Acetoxyphenyl)thio) ethyl}acetamide (NAP-TEA)

Procedure

Acetyl chloride method

To solution of N-{2-((4-Hydroxyphenyl)thio) ethyl}acetamide (200 mg, 0.95 mmol) in dry pyridine was added slowly acetyl chloride at −15° C. with stirring. The resulting solution was stirred at 25° C. for 1.5 hour. The residue obtained after removal of solvent was chromatographed on a low pressure silica gel column (CANAG, D-O, fine grain; Mobile phase: 5% MeOH/CHCl$_3$). The fractions containing product were collected and then the white powder obtained after removal of solvent was recrystallized to gain the white crystals from $H_2O$-MeOH. (Chemical yield: 217 mg, 0.85 mmol 90.3% ) mp=87°–88°

Characterization $^1$H NMR (Acetone-d$_6$): δ 7.52 (bro, s, 1H, NH), 7.41 (d, fine structure, 2H, J=8.5 Hz, aromatic C(2)-H, C(6)-H), 7.04 (d, fine structure 2H, J=8.5 Hz, aromatic C(3)-H, C(5)-H), 3.33 (m, 2H, J(CH$_2$—CH$_2$)=6 Hz, J(CH$_2$—NH)=7.5 Hz, CH$_2$C<u>H</u>$_2$NH), 3.05 (dd, 2H, J(CH$_2$—CH$_2$)=8 Hz, SC<u>H</u>$_2$), 2.22 (s, 3H, C<u>H</u>$_3$COO), 1.83 (s, 3H, C<u>H</u>$_3$CONH).

$^{13}$C NMR (Acetone-d$_6$) ppm; 169.95 (1C, CH$_3$<u>C</u>ONH) 169.29 (1C, CH$_3$<u>C</u>OO), 150.12 (1C, aromatic, C(4)), 133.61 (1C, aromatic, C(1)), 130.76 (2C, aromatic, <u>C</u>H) 122.98 (2C, aromatic, <u>C</u>H), 39.35 (1C, <u>C</u>H$_2$NH), 33.48 (1C, S<u>C</u>H$_2$), 22.52 (1C, <u>C</u>H$_3$CONH), 20.61 (1C, <u>C</u>H$_3$COO).

Exact mass calc. for $C_{11}H_{15}NO_3S$: 253.07725; found (HRMS), 253.0773; intensity=18.18%.

EXAMPLE 2B

Synthesis of N-{2-{(4-Acetoxyphenyl) thio}ethyl}propionamide (NAP-TEP)

A mixture of 2-ethyl-2-oxazoline (786 mg, 7.94 mmol) and 4-hydroxythiophenol (1 g, 7.94 mmol) was heated at 125° for 2 h under Ar gas. After cooling of the reaction mixture, the mixture was evaporated under vacuum. The residue was purified with a low pressure normal phase silica gel column chromatography (mobile phase: 10% MeOF in CHCl$_3$). N-propionyl-4-S-cysteaminylphenol (N-Pro-4-S-CAP) was obtained as a white powder on evaporation of the solvent (Chemical yield: 53.4%, 953 mg).

A mixture of N-propionyl-4-S-cysteaminylphenol, dry pyridine, and acetic anhydride is then stirred at 25° for 24 hours. The reaction mixture is evaporated under vacuum and the residue is purified with a low pressure normal phase silica gel column chromatography (mobile phase: 8% MeOH in CHCl$_3$). N-{2-{(4-acetoxyphenyl)thio}ethyl}-propionamide (NAP-TEP) is obtained as a white powder upon evaporation of the solvent.

EXAMPLE 3

In vivo covalent binding of ($^{14}$C)-N-acetyl-4-S-CAP was investigated in mice. Female C57BL/6J mice received a single intraperitoneal injection of 2.0 mmol/kg ($^{14}$C) -N-acetyl-4-S-CAP compound. The animals were killed 48 hours later. The tissues were removed and the covalent binding was determined as follows.

Five different tissues were examined for covalent binding of radioactively labelled N-acetyl-4-S-CAP intermediate(s). The maximum binding of N-acetyl-4-S-CAP was detected in the s.c. melanoma tumor and melanoma colony-bearing lung tissues. In contrast, the normal organs, e.g., the lung without melanoma colonies, kidney and liver, which are actively involved in drug metabolism of N-acetyl-4-S-CAP, did not reveal a significant accumulation of radioactive material. The results of such study are set out in the following Table 1.

TABLE 1

In Vivo Covalent Binding of (14C)-NACAP to Lung with and without B16F10 Melanoma Colonies, B16F10 Melanoma s.c. Tumor Tissue, Liver and Kidney

| Tissue[a] | Covalent Binding[b] (nmol covalently bound/mg of protein) |
|---|---|
| Lungs with B16F10 melanoma colonies | 0.330 ± 0.118 |
| Lungs without B16F10 melanoma colonies | 0.010 ± 0.001 |
| B16F10 melanoma s.c. tumor | 0.521 ± 0.076 |
| Liver | 0.013 ± 0.003 |
| Kidney | 0.008 ± 0.001 |

[a]Female C57BL/6I mice received a single intraperitoneal injection of 20 mmol/kg ($^{14}$C)-NACAP. The animals were killed 48 hr later, the tissues were removed, and the covalent binding was determined as described under above.
[b]The data are presented as the means + S.D. (n = 3).

In vivo biodistribution by whole-body autoradiography was determined in use of the compounds of this invention and in particular, ($^{14}$C)N-acetyl-4-S-CAP at 48 hours after i.p. injection of ($^{14}$C)N-acetyl-4-S-CAP in the mouse, radioactive material was cleared from the body and was not detectable in any normal organs except the lumen of the large intestine. A whole-body autoradiogram of the mouse with both an s.c. B16F10 melanoma tumor and a B16F10 lung melanoma colonies after single i.p. injection of ($^{14}$C) N-acetyl-4-S-CAP (5.0 µCi). 48 hours after injection the animal was killed, frozen and prepared for sectioning. The 20-µm sections were freeze-dried and exposed to x-ray film for whole-body autoradiography. A) A whole-body section without exposure to x-ray film. E, eye; B, brain; Lu, lung with B16F10 melanoma colonies; H, heart; Li, liver; Me, s.c. melanoma tumor; I, intestines. B) after exposure to x-ray film. Positive signal of accumulated radioactivity is clearly detectable in the melanoma colony-bearing lung and s.c. melanoma tissues, as well in the lumen of the distal partes of intestine. Bar, 1 cm.

This result demonstrates the significant detoxication of N-acetyl-4-S-CAP in the liver followed by the excretion of N-acetyl-4-S-CAP metabolites into the bile. The s.c. melanoma tumor and the lung with melanoma colonies were the only organs displaying a significant accumulation of the radioactivity.

The radiolabelled compounds of this invention and in particular, radiolabelled N-acetyl-4-S-CAP and radiolabelled NAP-TEA are particularly useful as radioimaging agents without causing toxic side effects in the host. Also, in appropriate dosages the compounds may be used effect radio-chemotherapy at specific melanoma sites within the host.

EXAMPLE 4

Experiments for O-Deacylation of NAP-TEA in Mouse Plasma

NAP-TEA was introduced to mouse plasma to determine by in vitro experimentation the extent to which NAP-TEA is deacetylated to form N-Acetyl-4-S-CAP. The procedure was as follows. Into 100 µl of mouse plasma, 10 µg of NAP-TEA was introduced. The mixture was shook for one-half of a minute and then passed through a Sep-Pak $C_{18}$ cartridge in either 7 ml of 5% methanol/water to form eluent 1 or in 4 ml of 50% methanol/water to form eluent 2. Both eluents 1 and eluents 2 were collected. Aqueous methanol was removed from eluent 2 to provide a residue which was subjected to HPLC under the following conditions. The HPLC had a column of µ Bonapak $C_{18}$ under reverse phase radical compression. The residue was mixed with methanol:water at 50:50 with a flow rate through the radiograph at 1 ml/min. The detector was a Water Associates Model 441 with detection by ultraviolet at 250 nm. All that was detected in eluent 2 as passed through the chromatograph was N-Acetyl-4-S-CAP which indicates that NAP-TEA was readily deacylated by the mouse plasma to give the desired active agent.

EXAMPLE 5

Determination of NAP-TEA, N-Acetyl-4-S-CAP and Metabolites in in vivo Experimentation A C57BL/6J Black Mouse was injected at 300 mg/kg body weight by i.p. administration of NAP-TEA. 100 µl of plasma was extracted from the mouse after 5 minutes of injection and after 20 minutes of injection. The plasma samples were treated in accordance with the procedure of Example 4. The plasma samples were passed through a Sep-Pak $C_{18}$ cartridge in either 5% methanol:water to produce eluent 1 or 50% methanol/water to produce eluent 2. Eluent 2 had the aqueous methanol removed therefrom to provide a residue. The residue was redissolved in methanol/ 0.1% acetic acid and water in a ratio of 50:50 and subjected to HPLC for both the 5 minute and 20 minute plasma samples. Their was no evidence of NAP-TEA but their was evidence of N-Acetyl-4-S-CAP. The concentration of N-Acetyl-4-S-CAP in the 5 minute extracted sample being considerably greater than in the 20 minute extracted sample to indicate that in vivo NAP-TEA is deacylated to N-Acetyl-4-S-CAP which in turn is then taken up by the mouse melanocytes.

EXAMPLE 6

In vitro Cytotoxicity of NAP-TEA

MTT assay in accordance with the standard procedure

MTT solution (Sigma catalog No. M2128) was dissolved in PBS at 1 mg/ml and filtered to sterilize the solution. The solution was stored in the dark at 4° C. until used. The growing cells were harvested, counted and inoculated into 96 well microtiter plates (1–2×10³ cells/well). After 24 h, drugs were applied to culture wells, and the cultures were incubated for 5 days at 37° C. At this time, 50 µl of MTT solution was added to microculture wells. After 4 h incubation at 37° C., supernatant was removed from each well. 150 µl of DMSO was added to solubilized the MTT-formazan product. After mixing gently, absorbance at 540 nm was measured with ELISA plate spectrophotometer.

Results

NAP-TEA showed lower in vitro cytotoxicity than that of N-Acetyl-4-S-CAP on 3 cell lines.

In vitro cytotoxicity($IC_{50}$) of NAP-TEA and N-Acetyl-4-S-CAP with MTT assay

| | Compound | |
|---|---|---|
| Cell line | NAP-TEA $IC_{50}$ | N-Acetyl-4-S-CAP |
| HeLa | 77 µg/ml | 75 µg/ml |
| SK-MEL-23 | 31 µg/ml | 25 µg/ml |
| UT amelanotic melanoma | 14 µg/ml | 12 µg/ml |

EXAMPLE 7

Utilization of NAP-TEA with Mushroom Tyrosinase

Procedure

A reaction mixture consisting of NAP-TEA (500 µmol) and of mushroom tyrosinase (11 units) in 1.0 ml of 0.05M sodium phosphate buffer (pH 6.8) was incubated at 37° C. in a water bath. The reaction was stopped periodically by cooling with ice. Aliquots removed at set time intervals were rapidly cooled to 0° C. in an ice bath and the remaining NAP-TEA was measured using HPLC.

HPLC instrument and conditions

Water 600 E liquid chromatograph system

Conditions: µBondapak $C_{18}$, Radial-Pak Cartridge (Waters)

Mobile phase: 70% MeOH/$H_2O$, 1 ml/min

Detector: Waters Model 441 UV absorbance detector

Detection. Wavelength 254 nm

Results

NAP-TEA was not a substrate of mushroom tyrosinase, due to the blocking effect of acetoxy group on the 4-position of the benzene ring because its concentration remained constant in the reaction mixture. However, the concentration of N-Acetyl-4-S-CAP in the reaction mixture dropped off rapidly over 25 minutes to almost zero amount after 50 minutes in the reaction mixture.

EXAMPLE 8

Melanocytotoxicity in vivo of NAP-TEA (Depigmentation of Black Hair)

Hairs were plucked manually from the back of 6–8 week old C57BL/6J black mice (4 mice). Starting on day 2, daily for 14 days NAP-TEA was injected i.p. The dose was 300 mg/kg body weight.

Results

After completion of the i.p. injections of NAP-TEA, mice were depigmented with the new replacement hair being almost pure white.

EXAMPLE 9

Depigmenting Effect of NAP-TEA on Newborn Black Mice

Six newborn (3 day old) C57BL/6J black mice were injected i.p. with a single dose of 0.1 mL of NAP-TEA solution (300 mg/kg body weight).

Results

The newborn mice were depigmented in all hair follicles with the growing hair being light grey after a single i.p. injection of NAP-TEA.

EXAMPLE 10

In vivo Melanocytotoxicity of NAP-TEA in Pig

Solutions of 15% NAP-TEA in DMSO(w/v) and of 15% NAP-TEA in 60% EtOH(w/v) were prepared for topical application to a Yucatan pig. NAP-TEA was applied to the back skin of the pig twice a day for 8 weeks. After 8 weeks, punch biopsy was performed from the application area and from normal skin. Specimens obtained were kept in 2N NaBr solution for 3 hours followed by separation of the epidermis from dermis. Specimens of epidermis were incubated for 3 hours in phosphate buffer (pH 7.4) containing L-Dopa. The specimens were fixed in 10% neutral formalin solution and then washed twice in PBS. Finally, the specimens were mounted in glycerol gel. The numbers of Dopa-positive melanocytes in 9 adjacent 1 mm$^2$ fields from each sample were counted.

Results

The fields from skin samples treated with NAP-TEA revealed a significant reduction in the number of functioning melanocytes;

|  | Number of functioning melanocytes (Average of 9 fields) |
|---|---|
| Normal epidermis | 166 ± 74/mm$^2$ |
| NAP-TEA in DMSO | 32 ± 14/mm$^2$ |
| NAP-TEA in 60% EtOH | 74 ± 25/mm$^2$ |
| DMSO only | 114 ± 56/mm$^2$ |
| EtOH only | 117 ± 38/mm$^2$ |

From the above specific examples, it is apparent that one of the preferred compounds, according to this invention, is converted in vivo to N-Acetyl-4-S-CAP which functions, as already discussed in applicant's co-pending International Application WO91/16302 as an excellent therapeutic agent in the treatment of pigmentary diseases. It is therefore understood that the acylated forms of the compounds of this invention are altered in vivo to yield compounds which already have been established as excellent therapeutic agents in the field of treating pigmentary disorders.

Throughout the specification we have referenced several Journal articles which relate to standard procedures and techniques. Those articles are listed as follows.

1. Alena F., Jimbow K. and Ito S. (1990) Melanocytotoxicity and Antimelanoma effects of Phenolic Amine Compounds in Mice in vivo. Cancer Res. 50, 3743.

2. Ito Y. and Jimbow K. (1987) Selective Cytotoxicity of 4-S-cysteaminylphenol on Follicular Melanocytes of the Black Mouse - Rational Basis for its Application to Melanoma Chemotherapy. Cancer Res. 47, 3278.

3. Inoue S., Ito S., Wakamatsu K., Jimbow K. and Fujita K. (1990) Mechanism of Growth Inhibition of Melanoma Cells by 4-S-cysteaminylphenol and its Analogues. Biochem. Pharmacol. 39, 1077.

4. Jimbow K., Iwashina T., Alena F., Yamada K., Pankovich J. and Umemura T. (1992) Exploitation of Pigment Biosynthesis Pathway as a Selective Chemotherapeutic Approach for Malignant Melanoma. J. Invest. Dermatol. (in press).

5. Miura S., Ueda T., Jimbow K., Ito S. and Fujita K. (1987) Synthesis of Cysteinylphenol, Cysteaminylphenol and Related Compounds, and in vivo Evaluation of Antimelanoma Effect. Arch. Dermatol. Res. 279, 219.

6. Miura T., Jimbow K. and Ito S. (1990) The in vivo Antimelanoma Effect of 4-S-cysteaminylphenol and its N-acetyl derivative. Int. J. Cancer 46, 931.

7. Pankovich, J. Jimbow K. and Ito S. (1990) 4-S-cysteaminylphenol and its Analogues as Substrates for Tyrosinase and Monoamine Oxidase. Pigment Cells Res. 3, 146.

8. Somayaji V. V., Wiebe. L. I. and Jimbow K. (1989) Experimental Antimelanoma Agents: The Synthesis of 4-S-cysteaminylphenol (U-$^{14}$C)phenol. Nuc. Compact 20, 158.

9. Wong M. and Jimbow K. (1991) Selective Cytotoxicity of N-acetyl-4-S-cysteaminylphenol on Follicular Melanocytes of Black Mice. Br. J. Dermatol 124, 56.

Although preferred embodiments of the invention are described herein in detail, it will be understood by those skilled in the art that variations may be made thereto without departing from the spirit of the invention or the scope of the appended claims.

I claim:

1. A process for radioimaging melanoma colonies in vivo in a subject comprising:

i) administering to the subject's circulatory system one or more radioimaging compounds selected from the group of compounds represented by the formula:

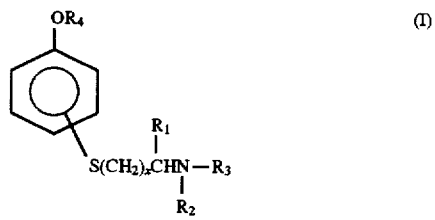

wherein $R_1$ is H or $C_1$–$C_8$ alkyl;

$R_2$ is H or $C_1$–$C_8$ alkyl;

$R_3$ is H, $C_1$–$C_8$ alkyl or $C_1$–$C_8$ alkanoyl;

$R_4$ is H or $C_1$–$C_8$ alkanoyl;

and wherein the compound of Formula (I) is radiolabelled with a radioactive element or a compound comprising a radioactive element and wherein said radioactive element or compound comprising a radioactive element 1) is covalently bound to the structure of formula (I);

2) is ionically associated with the structure of formula (I); or 3) is radioactive carbon which is part of the structure of formula (I); and x is 1 to 5, with the provisos that when x is 1, at least one of $R_1$, $R_2$ and $R_3$ is other than H, and that the sulphur containing group and the radioactive element or compound comprising a radioactive element are in the 2, 4 or 6 positions of the phenyl ring, and that the $R_2$ is $C_1$–$C_8$ alkyl when $R_4$ is $C_1$–$C_8$ alkanoyl; and ii) detecting the presence of emitted radiation from an accumulation of said selected radioimaging compound as said administered compounds binds solely to any melanoma tissue present in said subject.

2. A process for radiochemotherapy treatment of melanoma cells in a subject comprising:

I) administering to the subject's circulatory system one or more radiochemotherapy compounds selected from the group of compounds represented by the formula:

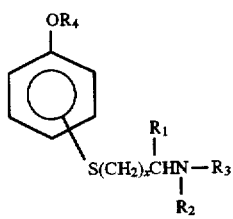

(I)

wherein $R_1$ is H or $C_1$–$C_8$ alkyl;

$R_2$ is H or $C_1$–$C_8$ alkyl;

$R_3$ is H, $C_1$–$C_8$ alkyl or $C_1$–$C_8$ alkanoyl;

$R_4$ is H or $C_1$–$C_8$ alkanoyl; ps and wherein the compound of Formula (I) is radiolabelled with a radioactive element or a compound comprising a radioactive element and wherein said radioactive element or compound comprising a radioactive element 1) is covalently bound to the structure of formula (I);

2) is ionically associated with the structure of formula (I); or 3) is radioactive carbon which is part of the structure of formula (I); and x is 1 to 5, with the provisos that when x is 1, at least one of $R_1$, $R_2$ and $R_3$ is other than H, and that the sulphur containing group and the radioactive element or compound comprising a radioactive element are in the 2, 4 or 6 positions of the phenyl ring, and that the $R_2$ is $C_1$–$C_8$ alkyl when $R_4$ is $C_1$–$C_8$ alkanoyl.

3. A process of claim 1 wherein said sulphur containing group is in the 4 position.

4. A process of claim 2 wherein said sulphur containing group is in the 4 position.

5. A process of claim 3 wherein said radioactive element or compound comprising a radioactive element is in the 2 or 6 position.

6. A process of claim 4 wherein said radioactive element or compound comprising a radioactive element is in the 2 or 6 position.

7. A process of claim 1 wherein said compounds are selected from compounds derived from N-acetyl-4-S-cysteaminylphenol, N,N-dimethyl-4-S-cysteaminylphenol, 4-S-homo-cysteaminylphenol, α-methyl-4-S-cysteaminylphenol, N,N-dimethyl{2-{(4'-acetoxyphenyl)thio}ethylamine or N-propionyl-4-S-cysteaminylphenol.

8. A process of claim 2 wherein said compounds are selected from compounds derived from N-acetyl-4-S-cysteaminylphenol, N,N-dimethyl-4-S-cysteaminylphenol, 4-S-homo-cysteaminylphenol, α-methyl-4-S-cysteaminylphenol, or N,N-dimethyl {2-{(4'-acetoxyphenyl)thio}ethylamine or N-propionyl-4-S-cysteaminylphenol.

9. A process of claim 7 wherein said compound is derived from N-acetyl-4-S-cysteaminylphenol.

10. A process of claim 8 wherein said compound is derived from N-acetyl-4-S-cysteaminylphenol.

* * * * *

UNITED STATES PATENT AND TRADEMARK OFFICE
CERTIFICATE OF CORRECTION

PATENT NO. : 5,756,068
DATED : May 26, 1998
INVENTOR(S) : KOWICHI JIMBOW

It is certified that error appears in the above-identified patent and that said Letters Patent is hereby corrected as shown below:

In the title on the title page and in column 1, change "THIOETER" to --THIOETHER--.

Claim 2 (column 19, line 15), delete "ps".

Signed and Sealed this

Eleventh Day of August 1998

Attest:

BRUCE LEHMAN

*Attesting Officer*  *Commissioner of Patents and Trademarks*